United States Patent [19]
Hipp et al.

[11] Patent Number: 5,707,340
[45] Date of Patent: Jan. 13, 1998

[54] DEVICE FOR CONNECTING AN ENDOSCOPE TO AN AUXILIARY APPARATUS

[75] Inventors: Klaus-Peter Hipp, Bretten; Klaus Schrumpf, Weingarten, both of Germany

[73] Assignee: Richard Wolf GmbH, Knittlingen, Germany

[21] Appl. No.: 559,102

[22] Filed: Nov. 16, 1995

[30] Foreign Application Priority Data

Dec. 10, 1994 [DE] Germany .................. 44 44 049.9

[51] Int. Cl.⁶ .................................................. A61B 1/04
[52] U.S. Cl. ........................ 600/112; 354/62; 285/314
[58] Field of Search .......................... 600/101, 109, 600/112, 174; 354/62; 285/314, 320, 308, 81; 403/328, 326, 315

[56] References Cited

U.S. PATENT DOCUMENTS

| | | | |
|---|---|---|---|
| 527,764 | 10/1894 | Bichet et al. | 285/314 |
| 2,102,774 | 12/1937 | Williams | 285/314 |
| 2,493,577 | 1/1950 | Franklin | 285/314 X |
| 4,305,386 | 12/1981 | Tawara | 600/112 |
| 4,318,395 | 3/1982 | Tawara | 600/112 |
| 4,844,071 | 7/1989 | Chen et al. | 600/112 |

FOREIGN PATENT DOCUMENTS

| | | |
|---|---|---|
| GM 6926837 | 11/1969 | Germany . |
| 23 46 197 A1 | 7/1975 | Germany . |
| GM 79 18 414 | 10/1979 | Germany . |
| 3541855 C2 | 12/1987 | Germany . |

*Primary Examiner*—Beverly M. Flanagan
*Attorney, Agent, or Firm*—Panitch Schwarze Jacobs & Nadel, P.C.

[57] ABSTRACT

There is disclosed a device which serves to connect an endoscope with an auxiliary apparatus, for example to a video camera, an objective or an ocular funnel. The device comprises a main body with a central recess for receiving the proximal end of the endoscope. Within the main body at least one lever is pivotably mounted, which juts into the central recess by an impinging spring force. This lever can be locked into the position in which it juts into the recess, by means of a clamping ring arranged on the main body.

7 Claims, 9 Drawing Sheets

DEVICE FOR CONNECTING AN ENDOSCOPE TO AN AUXILIARY APPARATUS

BACKGROUND OF THE INVENTION

The invention relates to a device for connecting an endoscope to an auxiliary apparatus.

DESCRIPTION OF THE PRIOR ART

Endoscopes are used in medicine to examine body cavities and, where necessary, to take pictures using an ocular positioned at the distal end of an endoscope with the eye or using an auxiliary apparatus e.g. a photo camera or video camera mounted on the ocular. Accordingly, the auxiliary apparatus is connected to the proximal end of the shaft (with insert funnel endoscopes) or with the ocular funnel of the endoscope.

In medical applications, various demands are made of this connection. On the one hand, the connection should be easily detachable, but on the other, any inadvertant detaching of the connection should be prevented. Moreover it is often necessary to allow radial twisting between the endoscope and the auxiliary apparatus. In other cases a torsional clamping may be desired. In both twistable condition and the clamped condition, where possible, the optical axes of the endoscope optic and an objective of the auxiliary apparatus should coincide.

There are many known devices which meet these requirements to varying degrees. The devices according to DE-GM 6926837 and 7918414 both have the provision of latching or clamping balls and a clamping ring, twistable against a spring force. On twisting the ring, the balls may be radially displaced into reliefs on the clamping ring (DE-GM 6926837) or axially in the proximal region, into recesses in the ring (DE-GM 7918414), allowing an ocular funnel of an endoscope to be inserted. When the clamping ring is again released and resiliently returns to its original position, the clamping balls are pressed against the ocular funnel which is then tightly fastened.

DE-C-3541855 also describes a device, on which clamping balls and a clamping ring are mounted, with the help of which an ocular funnel can be securely connected to the auxiliary apparatus. As described in DE-GM 6926837, the clamping balls may be displaced into reliefs on the inside of the clamping ring when the clamping ring is twisted against the spring force and an ocular funnel is inserted. In contrast to the device described in DE-GM 6926837, those reliefs described in DE-C-3541855 extend along the circumference in a manner such that they become deeper in the clockwise direction. With all known devices, however, after connecting the ocular section with the auxiliary apparatus, there is no free turning capacity, only a rigid fastening is possible.

Since the ocular funnels are arranged in the area around the eye, they often lack a suitable locating surface, and of course are not always manufactured with the precision which is desired for connecting an auxiliary apparatus. Since such auxiliary apparatus are increasingly used in applications, on the endoscope side, these requirements have been met. With regard to this, so called insert funnel endoscopes are known, for example from the catalogue page A13a, III.92 "CCD-Endocam" 5500 of Richard Wolf GmbH, in which the proximal end of the endoscope is specially designed for this purpose. This end is cylindrically designed with a circumferential groove, the shank being occluded by the ocular which is occluded flush with the outer circumference of the shank. For observation with the eye, an ocular funnel or a so called insert funnel is mounted; for observation with a camera on the other hand, an objective, an adapter, a camera or suchlike is mounted. The fastening of the insert funnel or the auxiliary apparatus to the proximal end of the shank is effected by way of an approximately radially guided screw, which initially effects a positive and furthermore a frictional fastening.

Although such fastening using screws has basically proven itself practically, in particular with regard to those previously mentioned techniques, it requires a particular finger tip dexterity to ensure the positive fastening of the auxiliary apparatus, but still allowing it to be twisted with regard to the endoscope. With frictional fastening, such as when tightening the screw or screws, care must be taken in order to prevent introducing too much force to one side, which may lead to a displacing of the optical axis.

SUMMARY OF THE INVENTION

Against this background, it is an object of the present invention to develop such types of devices for connecting an endoscope to an auxiliary apparatus, be it for the connection of the auxiliary apparatus with the ocular funnel, or with the shank end of the endoscope on the ocular side, which on the one hand provides for a simple and reliable handling, and on the other hand has a simple construction. In particular, the device should allow a locking on after insertion, as well as a twisting in this position. Moreover the latching and fastening must be effected in a simple manner with a minimum use of force.

In accordance with the invention this is achieved by those features specified in claim 1.

Auxiliary apparatus with regard to the present invention may include an objective, a camera or likewise, but also an insert funnel, for example for an insert funnel endoscope.

The solution according to the present invention provides for at least one, preferably three levers symmetrical to the central recess, jutting into the recess; the levers forced under a spring force in the pivoting direction towards the central recess, so that they displace under spring force on inserting the proximal end of the endoscope and then either grip behind the ocular funnel or with insert funnel endoscopes, into the groove at the proximal end of the shank, so that initially the device is latchably connected with the endoscope. The device according to the invention is then once initially secured against any inadvertant detaching of the endoscope, yet still rotatable. Only after turning the clamping ring arranged on the main body are the levers, in the position where they jut into the recess, impinged further by force and are locked. The fastening ring sits directly on the main body, and is therefore easily gripped and well accessible. With regard to the design of the length of the levers and their contours, as well as the inside contour of the clamping ring, the clamping force may be adjusted over a wide range, according to the hand force. The device can therefore be adapted to the practical requirements in an ideal manner. The arrangement of levers moreover provides for a very compact and at the same time stably built embodiment with little constuctional effort.

Preferably the levers are designed as rocker levers, i.e. with two lever arms, of which one lever arm, on one side is pivotable in the central recess and on the other side, for the purpose of locking, takes its bearing on the clamping ring, and the other lever arm is used for making the spring forces available. It is preferable to arrange a helical spring between this arm lever and the main body, which can deliver the desired spring force over large distances. Indeed this spring force should be relatively large, not only for fulfilling the previously described latching function, but also providing for the functional capabilities to be fulfilled in this latched position, i.e. that the optical axes of the endoscope and the auxiliary apparatus coincide. To guarantee the latter, with large tolerances between the proximal end of the endoscope and the central recess, it is useful to arrange three such rocker levers distributed symmetrically about the circumference, since the device is then automatically centred onto the endoscope.

It is preferable to arrange the pivoting axes of the rocker levers parallel to the longitudinal axis of the central recess, but these may also be arranged obliquely, for example in order that the force on placing the device onto the endoscope is smaller than that on removal. On the other hand, this effect may be compensated for by shaping the lever part which is pivotable into the recess.

In order to ensure as jerkless and even latching and unlatching as possible, and at the same time a centering in the axial direction, it is advantageous when that part of the lever which is pivotable in the recess is formed convexly, for example as part of an elliptical surface.

To prevent the clamping ring from unintentionally being removed from the device, it is mounted with a positive fit but rotatably on the main body. The design of this may be simply effected by screw connecting the clamping ring onto a supporting ring located between the clamping ring and the main body, the supporting ring being either fastened with a positive fit directly on the carrying body or for example by holding it onto the main body using fastening screws which jut into a groove in the main body.

To ensure that the clamping ring is only brought into the locked position when this is actually desired, it is useful to provide a latching device between the clamping ring and the main body, which latchably fastens the clamping ring in its unlocked position. A certain amount of resistance must then be overcome before this clamping ring can be moved out of this position. Reversably, on unlocking, by latching the clamping ring, it can be ensured when this position is reached.

A further advantage of the invention, in addition to those previously mentioned, comprises appropriately dimensioning the rocker lever allowing endoscopes of significantly differing diameters to be accomodated. Moreover, the design according to the present invention guarantees a particularly reliable and simple handling. The simple construction provides for an easy assembly and an easy replacement of individual parts.

BRIEF DESCRIPTION OF THE DRAWINGS

The invention is hereinafter described in more detail by means of one embodiment of the invention represented in the drawings. These show.

DETAILED DESCRIPTION OF THE PREFERRED EMBODIMENTS

The device illustrated in FIGS. 1 to 12 comprises essentially a main body 2 with countersinkings 32, three rocker levers 3, three springs 4 and a clamping ring 5.

Each of three symmetrical bores 6 are made obliquely to the radius in the main body. Helical springs 4 are inserted into the bores 6, the ends of which repectively support the rocker lever 3. Each of the rocker levers comprises a bore 8 through which a peg 9 is inserted as a pivot. As can be seen from FIG. 2, each peg is pressed into a bore made in the main body parallel to the axis and therefore is fixed into its position.

Figure 2:
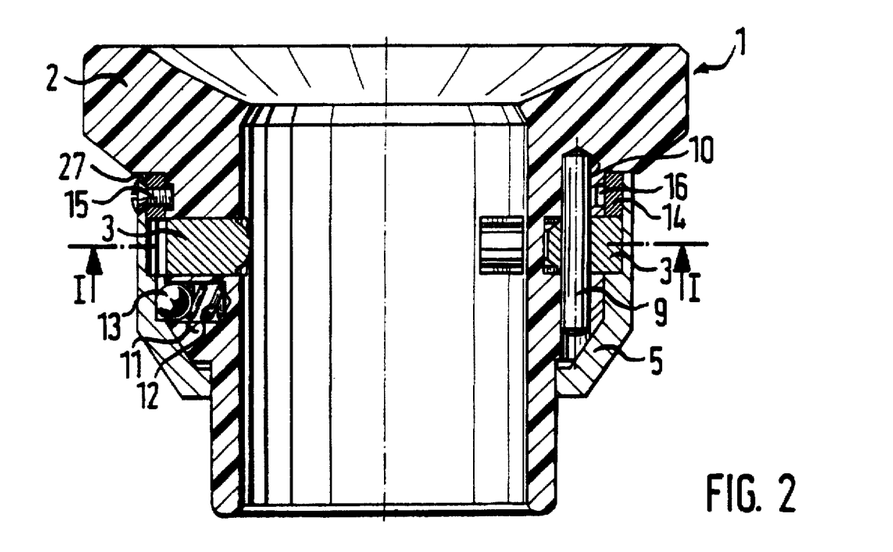

On the distal side of the rocker levers 3, the main body is provided with three further bores 11, one of which is shown in FIG. 2, into which is inserted one after the other, a helical spring 12 and a latching ball 13. The latching balls 13 may latch into reliefs 26 of the clamping ring 5 as described later.

On the proximal side of the rocker lever 3, between the clamping ring 5 and the main body 2, a supporting ring is inserted. The clamping ring 5 and the supporting ring 14 are provided with recesses 27 which are alligned to one another, and are connected to one another here with screws. In this region, the main body is provided with a non-circumferential groove 16, which serves as a stop for the screw 15, which serves to limit rotational movement, and into which the ends of the screws 15 project, so that the rotatability of the clamping ring with regard to the main body is limited, and the clamping ring is positively connected with the main body.

Figure 3:
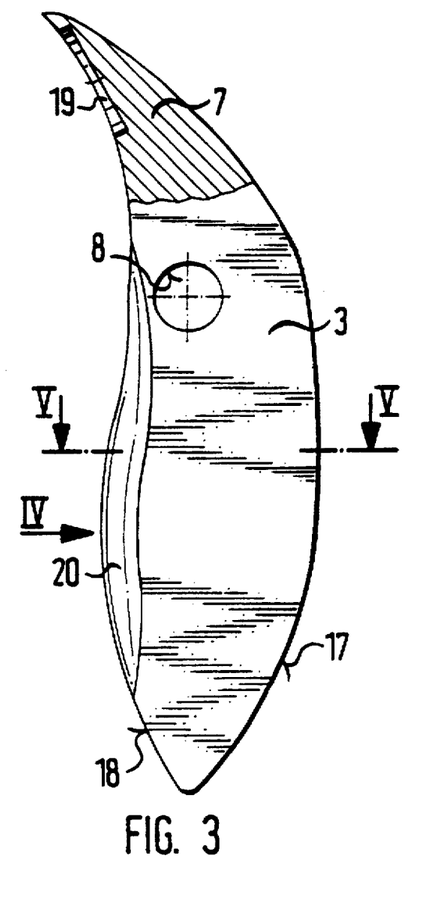
Figure 4:
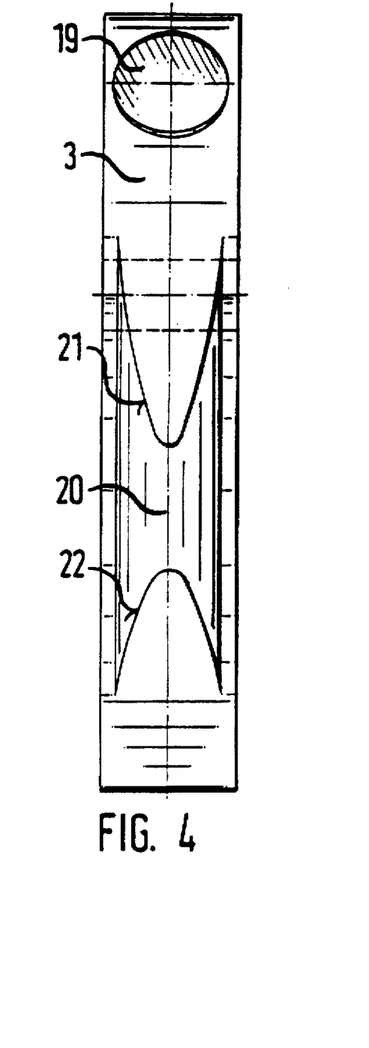
Figure 5:
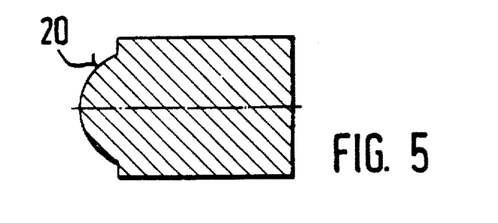

FIGS. 3 to 5 illustrate the details of the rocker lever. These are pointed at both ends, and comprise a curved outer arc 17 and an approximately S-shaped inner arc 18. On its end which is supported by the spring 4, blind hole type reliefs 19 are provided, in which the ends of the springs lie (see FIG. 1). The above mentioned bore 8 can be seen in FIG. 3. On one part of the side profile of the inner arc 18 a projection 20 is provided, the form of which is shown in FIG. 4. The parabola shaped lines 21 and 22 shown that the projection increases towards the apex and between the apexes the size remains constant. In FIG. 5 a section through the rocker lever along the line V—V of FIG. 3 is shown, where the projection has reached its complete height. Furthermore it can be seen that the projection in the region between the apexes has a circular arc shape.

Figure 6:
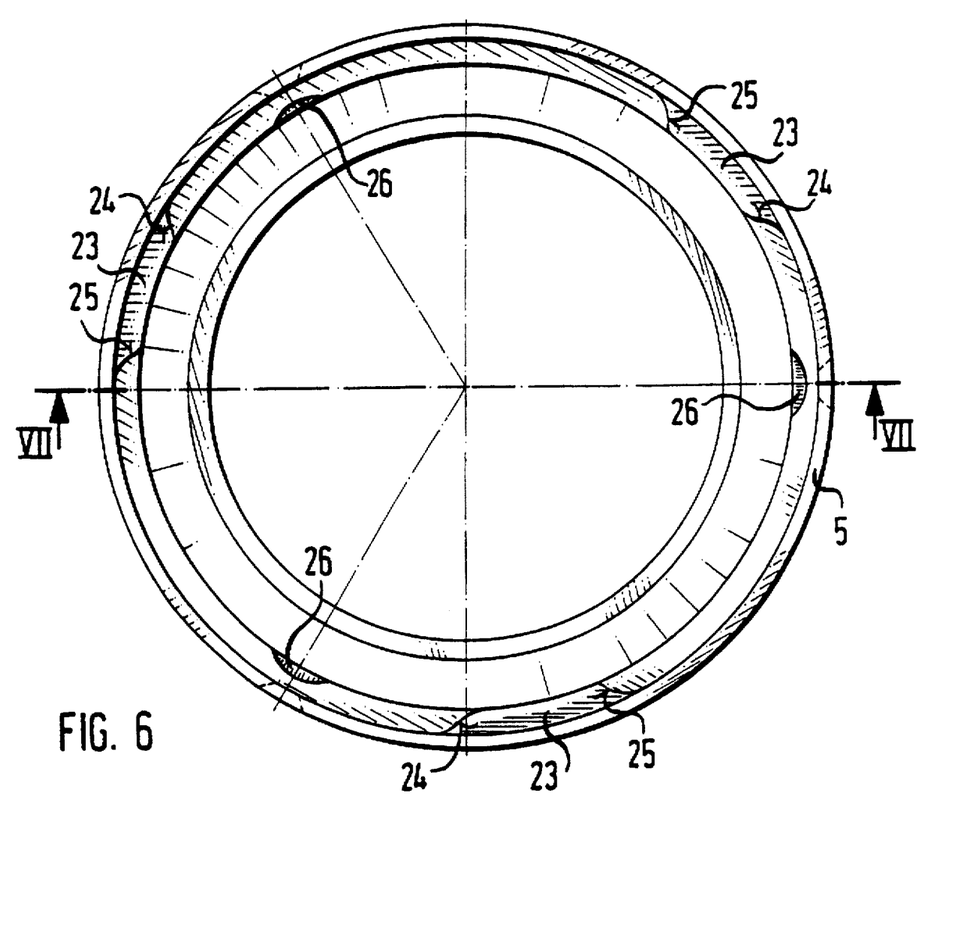
Figure 7:
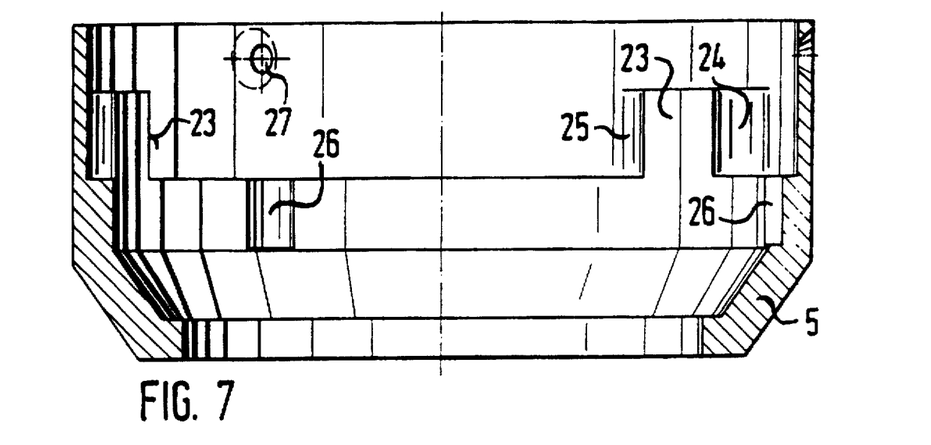

The clamping ring is shown in detail in FIGS. 6 and 7. The lugs 23 which project inwardly comprise an S-shaped shoulder 24 and a curved shoulder 25. Distally of the lugs are located the above mentioned reliefs 26 for receiving the latching balls. Moreover the clamping ring 5 comprises, as desribed above, a recess 27 for screwing in the screw 15.

Figure 9:
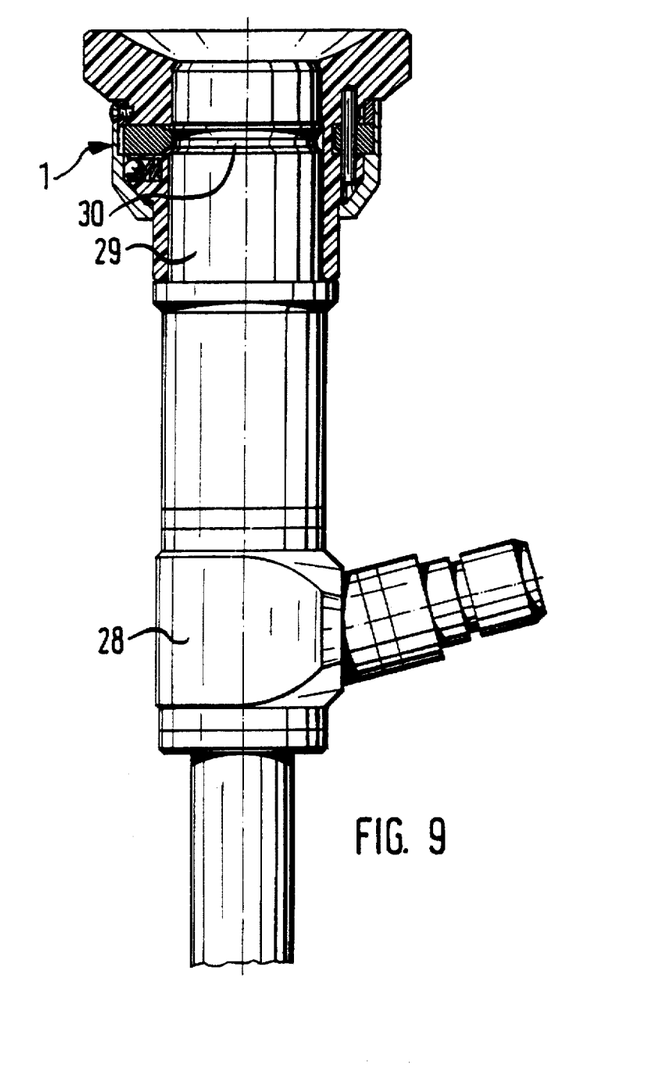
Figure 11:
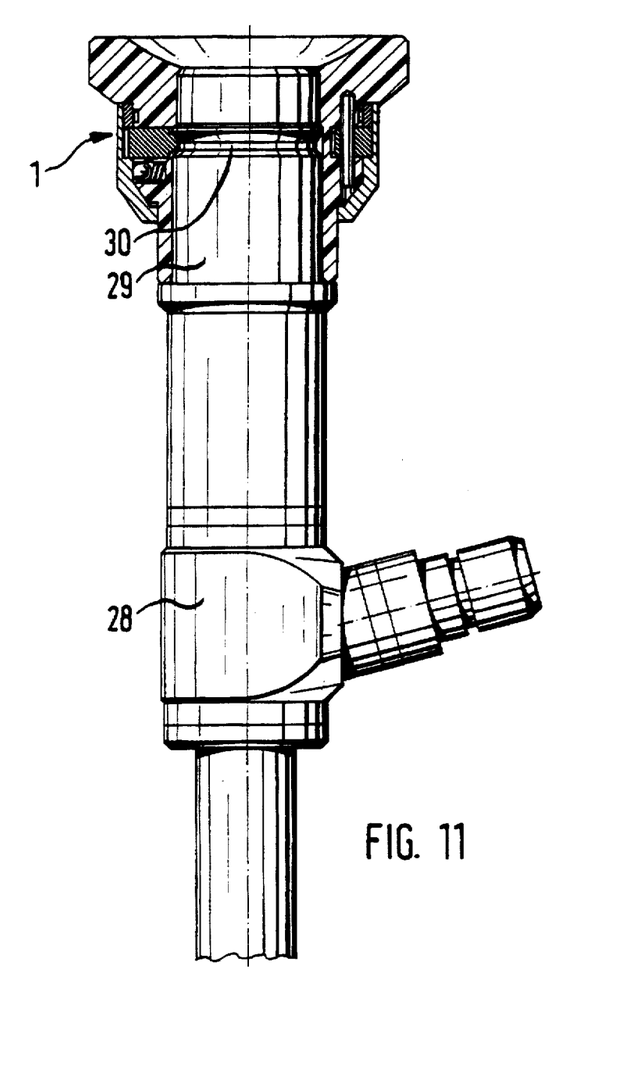
Figure 12:
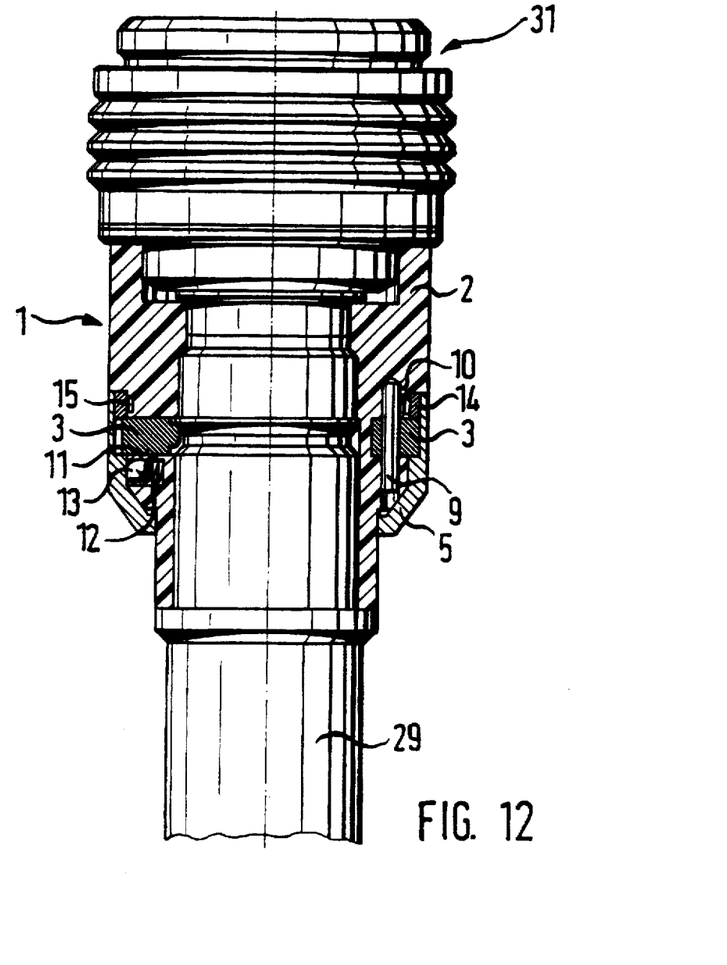

As is shown in FIGS. 9 and 11, an endoscope 28, to be inserted into the device. 1, comprises a circumferential groove 30 on its shank 29.

Figure 1:
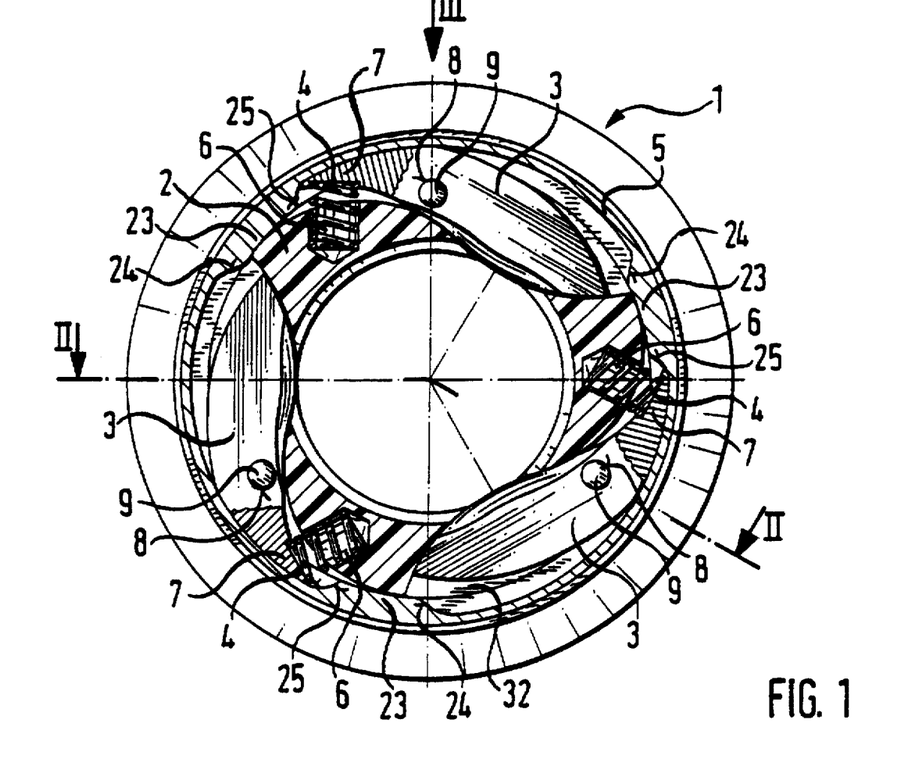
FIG. 1 a cross-section through the device according to the invention along line I—I in FIG. 2, FIG. 2 a longitudinal section through the device along the line II—II in FIG. 1, FIG. 3 an enlarged view of the rocker lever according to FIG. 1, FIG. 4 a side view in the direction of arrow IV in FIG. 3, FIG. 5 a cross-section along the line V—V in FIG. 3, FIG. 6 an enlarged view of a plan view of the clamping ring of the device according to FIG. 1, FIG. 7 a cross-section along the line VII—VII in FIG. 6, FIG. 8 the device as shown in FIG. 1 with the proximal part of an inserted endoscope in the latched position, FIG. 9 a longitudinal section according to FIG. 2 of the device according to FIG. 8, FIG. 10+11 the device illustrated according to FIGS. 8 and 9, but in the clamped position, FIG. 12 a longitudinal section of the device according to the invention on an objective, with the endoscope shank, FIG. 1a, 1b and 3a to 7a a further embodiment of the device according to the invention with a turning ring operating in the reverse direction illustrated according to FIGS. 1 and 3 to 7.

FIGS. 1 and 2 show the position in which no endoscope has been inserted. As such, part of the projection 20 on the rocker lever projects into the cylindrical inner chamber of the main body 2.

Figure 8:
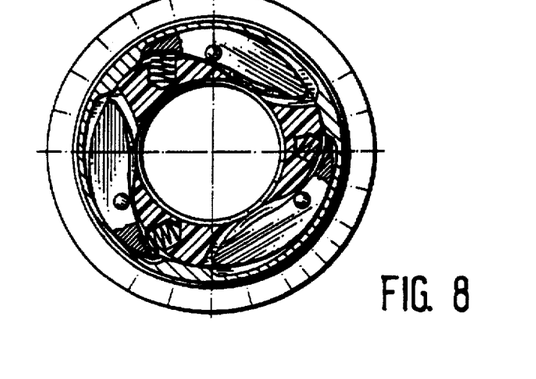

In this position the rocker lever 3, by radial pressure on its projection 20 on the inner arc 18, exerted by inserting an endoscope, may pivot freely over a certain amount about the peg 9 inserted into the main body, and thus completely clears the cylindrical opening in the main body 2. On its opposite end 7, the rocker lever is supported on the spring 4 by which means, the rocker lever is pressed into the groove 30 of the endoscope 28 when the shank 29 is completely inserted, in which the groove 30 is located at the same height as the rocker lever 3. The latching position as shown in FIGS. 8 and 9 is then reached.

In this position, the clamping ring 5 is fixed by the latching balls 13, which are pressed by springs 12 into the respective reliefs 26 in the clamping ring.

Figure 10:
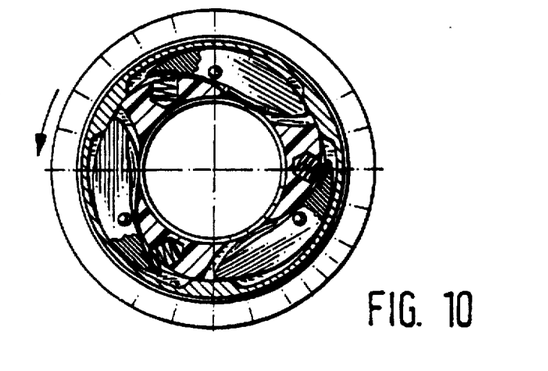

If, when the endoscope has been inserted, the clamping ring 5 is rotated anti-clockwise, as shown in FIGS. 10 and 11, the lugs 23 of the clamping ring 5 slide over the outer arcs of the rocker levers and push these radially inwardly without resilience, by which means, the projections 20 of the rocker levers are pressed increasingly against the groove 30 on the endoscope 28, the more the clamping ring 5 is rotated.

The outer arcs 17 of the rocker levers 3 are designed such that by self locking, any self-acting detachment is prevented. For releasing the endoscope, the clamping ring 5 is rotated clockwise in its home position, in which it is noticably latched by the spring force impinging on the latching balls 13. The endoscope 28 can then be pulled out.

The device according to the invention is herinafter described by way of an ocular funnel, which is used with insert funnel endoscopes. It can be understood that this device can be used for any appliance which can be connected to the endoscope, such as for example a video camera, objective, adapter for stereo ocular etc., such as illustrated for example by FIG. 12. Here the objective 31 is illustrated, which is connected with the endoscope shank 29 in an analog manner. It can be clearly seen that the main body 2 in the region of the latching-clamping device is identical with that of the main body of the insert funnel, which is made clear by a comparison of FIGS. 2 and 12.

Figure 3A:
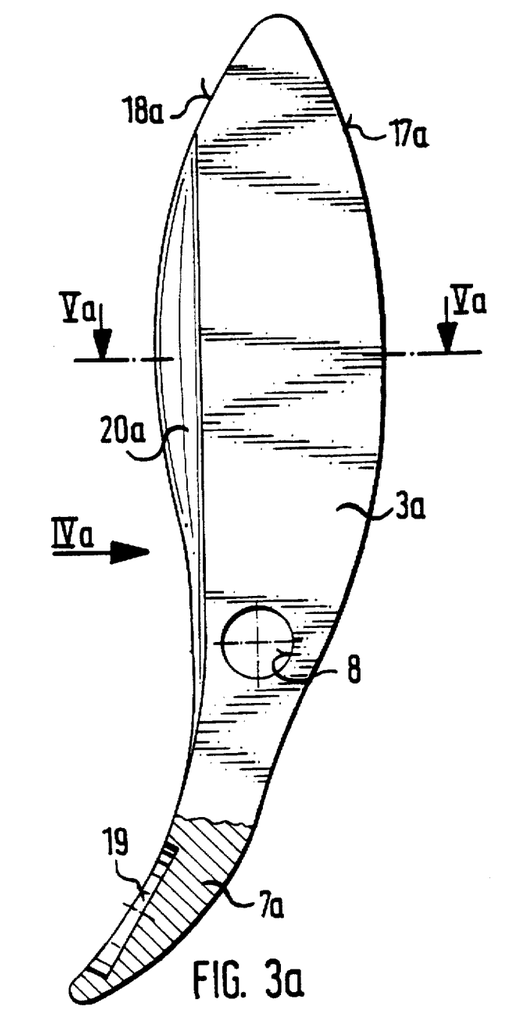
Figure 4A:
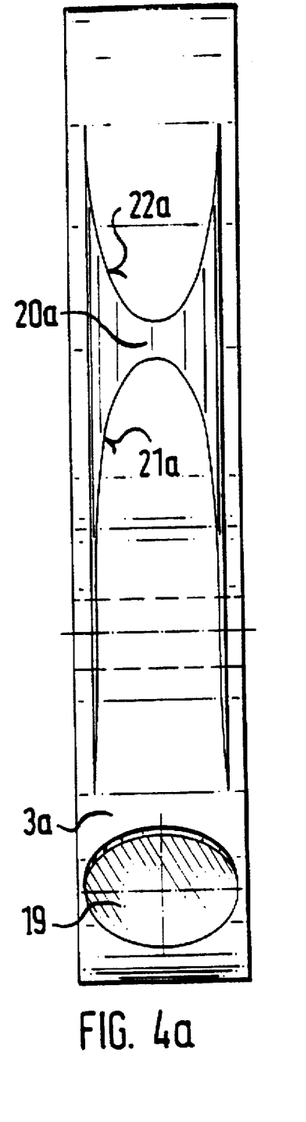
Figure 5A:
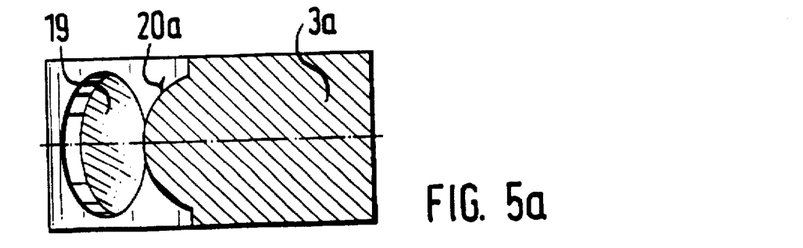
Figure 6A:
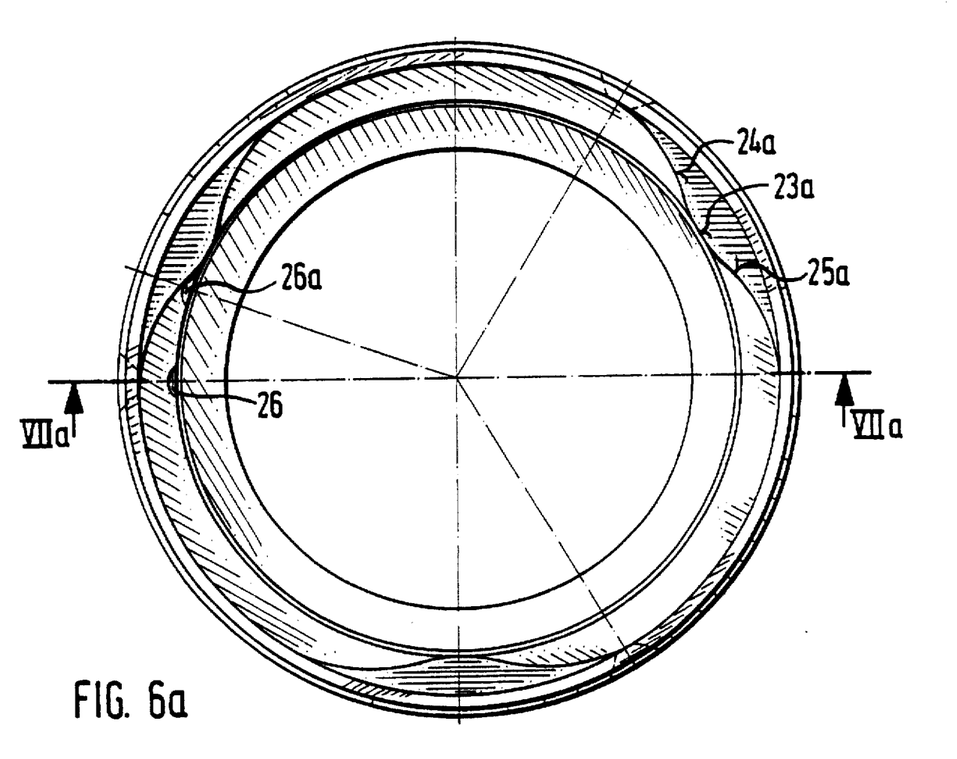
Figure 7A:
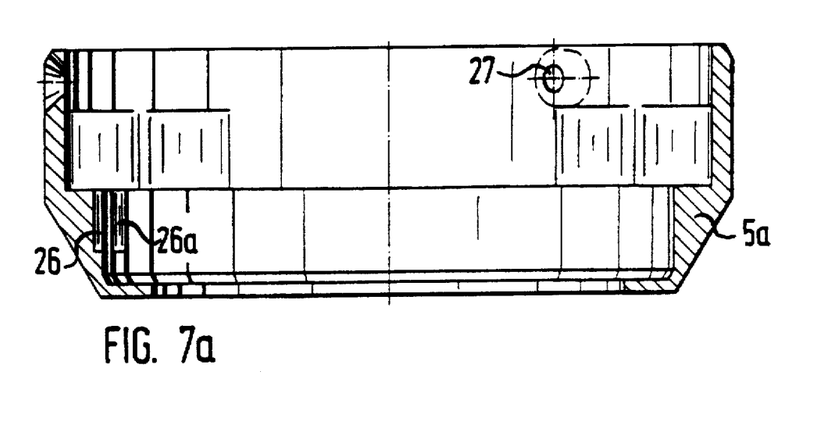

The device illustrated by way of FIGS 1a, 1b and 3a to 7a differs essentially from those previously described, in that the clamping ring 5a works in the opposite rotational direction, and the design of the rocker levers 3a has been accordingly modified. It has been refrained from describing this embodiment in detail, those components which identically correspond to those previously described have been given the same reference numerals. Those components which are specially adapted for the opposite rotational direction, have the same reference numeral but with addition a. With this embodiment, rotating the clamping ring clockwise effects the locking of the shank, and in comparison to those previous embodiments, a stronger clamping effect is achieved. FIGS. 3a, 4a and 5a illustrate the shape of the rocker lever 3a which are required for these variations, the FIGS. 6a and 7a show the corresponding design of the clamping ring 5a.

Figure 1A:
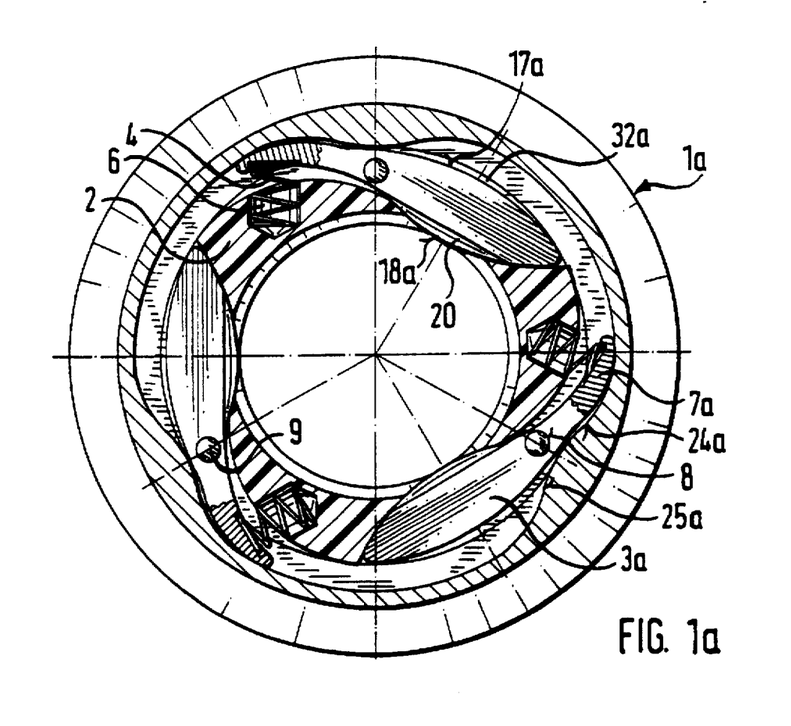
Figure 1B:
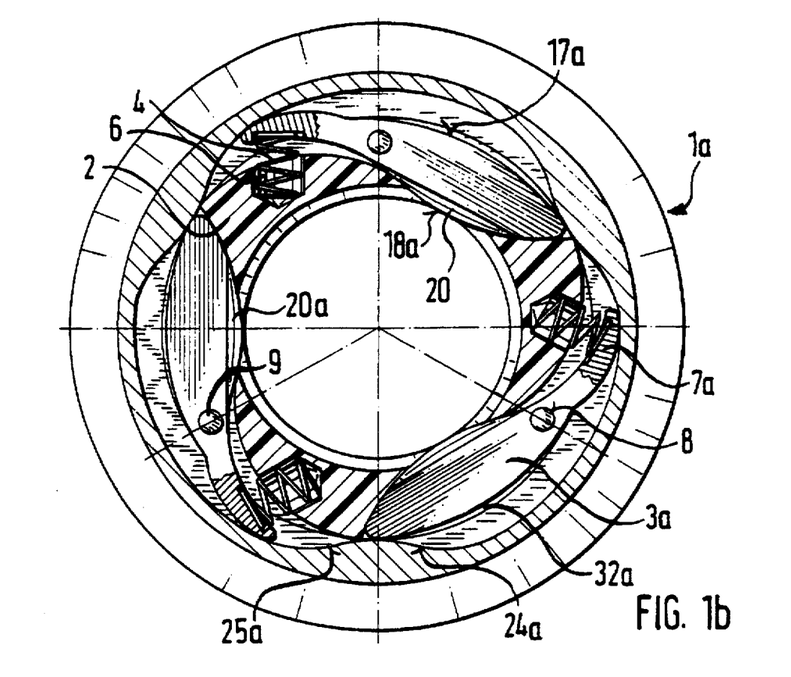

In the latched position illustrated in FIG. 1a, the lugs 23a of the clamping ring 5a are located directly above the pivoting axes 9 of the rocker lever 5a. With a corresponding design of the outer arc 17a of the rocker levers 3a, these are, in this shown latched position, freely pivotable about their pivoting axes. By turning the clamping ring 5a in the clockwise direction its lugs 23a a glide over the outer arcs 17a of the rocker levers 3a and press these inwards, as with the previously mentioned embodiments. It must be underlined that with this variation, with increased turning of the clamping ring 5a in the clockwise direction, the resulting clamping force on the projection 20a of the rocker lever 3a, by way of an improved leverage between the pivoting axis and pressure point, is increased even further compared to that of the previous described embodiments.

Whereas in the embodiments according to FIGS. 1 to 12, a latched position is envisaged, in which the three latching balls 13 latch into the reliefs 26, the variations described by way of FIGS. 6a and 7a provide for only one relief 26 for each latched position and accordingly only one latching ball 13. However within the clamping ring 5a, there are arranged two such reliefs 26 angularly seperated by approx. 20°. This further relief 26 permits a second latched position in which the rocker levers 3a are not yet locked, but on the other hand can no longer pivot out, so that a shank which is then inserted into the device is locked with a positive fit, but is still rotatable. In comparison to the first latched position, in the intermediate position, any inadvertent detaching of the endoscope and auxiliary apparatus can be reliably prevented, even when large axial forces are introduced.

We claim:

1. A device for connecting endoscope to an auxiliary apparatus, comprising a main body (2) with a central recess for receiving a proximal endoscope end (28), at least one lever (3) pivotably mounted in the main body (2), said lever jutting into the central recess under a spring force, a clamping ring (5) arranged on the main body (2) for urging the at least one lever into a locked position in which it juts into the central recess, and a supporting ring (14) arranged between the clamping ring (5) and the main body (2), the clamping ring (5) being fixed on the main body (2) by the supporting ring with a screw attachment and positive fit.

2. The device according to claim 1, wherein the at least one lever is designed as a rocker lever (3) having a first lever arm on one side of the pivot axis, which is pivotable into the central recess and a second lever arm on another side of the pivot axis for locking by bearing against the clamping ring, the second lever arm (7) being supported on the main body (2) by a spring.

3. The device according to claim 2, wherein the first lever arm is formed convexly on a side facing the central recess.

4. The device according to claim 1, comprising three rocker levers (3) arranged on the main body (2) symmetrically distributed about a circumference of the central recess.

5. The device according to claim 1, wherein the clamping ring (5) is rotatably mounted on the main body.

6. The device according to claim 1, further comprising between the main body (2) and the clamping ring (5), a latching device (11,12,13,26) with which the clamping ring (5) is latchable in an unlocked position.

7. The device according to claim 6, wherein the latching device (11,12,13, 26) comprises two latched positions, such that in one latched position a shank (29) of an endoscope inserted into the device may be fixed with a positive fit, but rotatably fixed.

* * * * *